United States Patent
Castro

(10) Patent No.: US 12,318,094 B2
(45) Date of Patent: Jun. 3, 2025

(54) CLIP APPLIER

(71) Applicant: TELEFLEX MEDICAL INCORPORATED, Morrisville, NC (US)

(72) Inventor: Salvatore Castro, Raleigh, NC (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 706 days.

(21) Appl. No.: 17/513,022

(22) Filed: Oct. 28, 2021

(65) Prior Publication Data

US 2022/0047269 A1    Feb. 17, 2022

Related U.S. Application Data

(63) Continuation of application No. PCT/US2020/052746, filed on Sep. 25, 2020.

(60) Provisional application No. 62/906,585, filed on Sep. 26, 2019.

(51) Int. Cl.
*A61B 17/128*    (2006.01)
*A61B 17/00*    (2006.01)

(52) U.S. Cl.
CPC .. *A61B 17/128* (2013.01); *A61B 2017/00367* (2013.01); *A61B 2017/00986* (2013.01)

(58) Field of Classification Search
CPC ........ A61B 17/128; A61B 2017/00367; A61B 2017/00986; A61B 17/1227; A61B 17/1285; A61B 17/122; A61B 17/07207; A61B 17/10; A61B 2017/12004; A61B 17/30; A61B 2017/2937; A61B 2017/2933; A61B 17/320016

See application file for complete search history.

(56) References Cited

U.S. PATENT DOCUMENTS

| | | | |
|---|---|---|---|
| 929,868 A | 8/1909 | Mueller |
| 1,482,290 A | 1/1924 | Elzi |
| 1,728,322 A | 9/1929 | Badrian |
| 2,384,697 A | 9/1945 | Riccardi |

(Continued)

FOREIGN PATENT DOCUMENTS

| AU | 676836 B2 | 3/1997 |
|---|---|---|
| CN | 1356092 A | 7/2002 |

(Continued)

*Primary Examiner* — Brooke Labranche
*Assistant Examiner* — Aman Kumar Mann
(74) *Attorney, Agent, or Firm* — BakerHostetler

(57) ABSTRACT

A clip applier may be configured to apply a surgical clip. The clip applier may include a first jaw member and a second jaw member, where the first jaw member is configured to pivot between an open configuration and a closed configuration. The clip applier may also include a first leaf spring configured to bias the first jaw member into the open configuration, and a tubular member configured to advance over the first jaw member to cam the first jaw member into a closed configuration against the bias of the first leaf spring. The clip applier may further include a second leaf spring configured to bias the second jaw member into the open configuration, and a tubular member configured to advance over the second jaw member to cam the second jaw member into a closed configuration against the bias of the second leaf spring.

18 Claims, 5 Drawing Sheets

(56) References Cited

U.S. PATENT DOCUMENTS

| | | |
|---|---|---|
| 2,594,102 A | 4/1952 | Vollmer |
| 2,598,901 A | 6/1952 | Garland |
| 2,626,608 A | 1/1953 | Garland |
| 2,635,238 A | 4/1953 | Garland |
| 2,744,251 A | 5/1956 | Vollmer |
| 2,813,269 A | 11/1957 | Jacobs |
| 2,814,222 A | 11/1957 | Sanders |
| 2,881,762 A | 4/1959 | Lowrie |
| 2,890,519 A | 6/1959 | Storz, Jr. |
| 3,032,039 A | 5/1962 | Beaty |
| 3,150,379 A | 9/1964 | Brown |
| 3,172,133 A | 3/1965 | Rizzo |
| 3,351,191 A | 11/1967 | Mallina |
| 3,446,212 A | 5/1969 | Le Roy |
| 3,463,156 A | 8/1969 | McDermott et al. |
| 3,503,396 A | 3/1970 | Pierie et al. |
| 3,503,397 A | 3/1970 | Fogarty et al. |
| 3,503,398 A | 3/1970 | Fogarty et al. |
| 3,713,533 A | 1/1973 | Reimels |
| 3,766,925 A | 10/1973 | Rubricius |
| 3,825,012 A | 7/1974 | Nicoll |
| 3,827,438 A | 8/1974 | Kees |
| 3,867,944 A | 2/1975 | Samuels |
| 3,874,042 A | 4/1975 | Eddleman et al. |
| 3,954,108 A | 5/1976 | Davis |
| 4,076,120 A | 2/1978 | Carroll et al. |
| 4,120,302 A | 10/1978 | Ziegler |
| 4,274,415 A | 6/1981 | Kanamoto et al. |
| 4,316,468 A | 2/1982 | Klieman et al. |
| 4,325,376 A | 4/1982 | Klieman et al. |
| 4,337,774 A | 7/1982 | Perlin |
| 4,344,531 A | 8/1982 | Giersch |
| 4,345,600 A | 8/1982 | Rothfuss |
| 4,346,869 A | 8/1982 | MacNeill |
| 4,390,019 A | 6/1983 | Leveen et al. |
| 4,394,864 A * | 7/1983 | Sandhaus ............... A61F 6/204 |
| | | 606/221 |
| 4,414,721 A | 11/1983 | Hufnagel |
| 4,418,694 A | 12/1983 | Beroff et al. |
| 4,428,374 A | 1/1984 | Auburn |
| 4,444,187 A | 4/1984 | Perlin |
| 4,450,840 A | 5/1984 | Mericle et al. |
| 4,458,682 A | 7/1984 | Cerwin |
| 4,471,780 A | 9/1984 | Menges et al. |
| 4,476,865 A | 10/1984 | Failla et al. |
| 4,487,204 A | 12/1984 | Hrouda |
| 4,487,205 A | 12/1984 | Di et al. |
| 4,492,232 A | 1/1985 | Green |
| 4,509,517 A * | 4/1985 | Zibelin ............... A61B 17/29 |
| | | 606/127 |
| 4,519,392 A | 5/1985 | Lingua |
| 4,527,562 A | 7/1985 | Mericle |
| 4,534,351 A | 8/1985 | Rothfuss et al. |
| 4,550,729 A | 11/1985 | Cerwin et al. |
| 4,570,633 A | 2/1986 | Golden |
| 4,579,118 A | 4/1986 | Failla |
| 4,588,160 A | 5/1986 | Flynn et al. |
| 4,589,626 A | 5/1986 | Kurtz et al. |
| 4,616,651 A | 10/1986 | Golden |
| 4,638,804 A | 1/1987 | Jewusiak |
| 4,671,281 A | 6/1987 | Beroff et al. |
| 4,686,983 A | 8/1987 | Leisman et al. |
| 4,712,549 A | 12/1987 | Peters et al. |
| 4,716,886 A | 1/1988 | Schulman et al. |
| 4,726,372 A | 2/1988 | Perlin |
| 4,807,622 A | 2/1989 | Ohkaka et al. |
| 4,822,348 A | 4/1989 | Casey |
| 4,834,090 A | 5/1989 | Moore |
| 4,834,096 A | 5/1989 | Oh et al. |
| 4,854,317 A | 8/1989 | Braun |
| 4,870,965 A | 10/1989 | Jahanger |
| 4,919,152 A | 4/1990 | Ger |
| 4,924,864 A | 5/1990 | Danzig |
| 4,934,364 A | 6/1990 | Green |
| 4,936,447 A | 6/1990 | Peiffer |
| 4,938,764 A | 7/1990 | Glaberson |
| 4,938,765 A | 7/1990 | Rasmusson |
| 4,942,886 A | 7/1990 | Timmons |
| 4,950,275 A | 8/1990 | Donini |
| 4,961,499 A | 10/1990 | Kulp |
| 4,972,949 A | 11/1990 | Peiffer |
| 4,976,722 A | 12/1990 | Failla |
| 5,002,552 A | 3/1991 | Casey |
| 5,009,657 A | 4/1991 | Cotey et al. |
| 5,026,382 A | 6/1991 | Peiffer |
| 5,046,611 A | 9/1991 | Oh |
| 5,047,038 A | 9/1991 | Peters et al. |
| 5,053,045 A | 10/1991 | Schmidt et al. |
| 5,062,846 A | 11/1991 | Oh et al. |
| 5,078,731 A | 1/1992 | Hayhurst |
| 5,100,416 A | 3/1992 | Oh et al. |
| 5,104,395 A | 4/1992 | Thornton et al. |
| 5,112,343 A | 5/1992 | Thornton |
| 5,127,915 A | 7/1992 | Mattson |
| 5,141,514 A | 8/1992 | Van Amelsfort |
| 5,160,339 A | 11/1992 | Chen et al. |
| 5,163,945 A | 11/1992 | Ortiz et al. |
| 5,171,251 A | 12/1992 | Bregen et al. |
| 5,171,252 A | 12/1992 | Friedland |
| 5,172,700 A * | 12/1992 | Bencini ............... A61B 10/06 |
| | | 600/564 |
| 5,201,416 A | 4/1993 | Taylor |
| 5,207,692 A | 5/1993 | Kraus et al. |
| 5,234,449 A | 8/1993 | Bruker et al. |
| 5,246,450 A | 9/1993 | Thornton et al. |
| 5,259,405 A | 11/1993 | Hua-Chou |
| 5,279,416 A | 1/1994 | Malec et al. |
| 5,318,589 A * | 6/1994 | Lichtman ............... A61B 17/29 |
| | | 606/205 |
| 5,330,442 A | 7/1994 | Green et al. |
| 5,330,487 A | 7/1994 | Thornton et al. |
| 5,366,458 A | 11/1994 | Korthoff et al. |
| 5,405,344 A | 4/1995 | Williamson et al. |
| 5,431,668 A | 7/1995 | Burbank et al. |
| 5,462,555 A | 10/1995 | Bolanos et al. |
| 5,464,416 A | 11/1995 | Steckel |
| 5,487,746 A | 1/1996 | Yu et al. |
| 5,501,693 A | 3/1996 | Gravener |
| 5,509,920 A | 4/1996 | Phillips et al. |
| 5,549,621 A | 8/1996 | Bessler et al. |
| 5,569,274 A | 10/1996 | Rapacki et al. |
| 5,575,796 A | 11/1996 | King et al. |
| 5,575,802 A | 11/1996 | McQuilkin et al. |
| 5,591,178 A | 1/1997 | Green et al. |
| 5,607,436 A | 3/1997 | Pratt et al. |
| 5,626,585 A | 5/1997 | Mittelstadt et al. |
| 5,667,516 A | 9/1997 | Allen |
| 5,697,938 A | 12/1997 | Jensen et al. |
| 5,700,270 A | 12/1997 | Peyser et al. |
| 5,713,911 A | 2/1998 | Racenet et al. |
| 5,713,912 A | 2/1998 | Porter |
| 5,722,982 A | 3/1998 | Ferreira et al. |
| 5,725,542 A | 3/1998 | Yoon |
| 5,797,922 A | 8/1998 | Hessel et al. |
| 5,810,853 A | 9/1998 | Yoon |
| 5,833,696 A | 11/1998 | Whitfield et al. |
| 5,843,097 A | 12/1998 | Mayenberger et al. |
| 5,846,255 A | 12/1998 | Casey |
| 5,908,430 A | 6/1999 | Appleby |
| 5,921,991 A | 7/1999 | Whitehead et al. |
| 5,925,052 A | 7/1999 | Simmons |
| 5,954,731 A | 9/1999 | Yoon |
| 5,972,003 A | 10/1999 | Rousseau et al. |
| 5,976,161 A * | 11/1999 | Kirsch ............... A61B 17/11 |
| | | 606/205 |
| 5,997,548 A | 12/1999 | Jahanger |
| 6,010,516 A | 1/2000 | Hulka |
| 6,013,088 A | 1/2000 | Karavidas |
| 6,015,417 A | 1/2000 | Reynolds, Jr. |
| 6,050,996 A | 4/2000 | Schmaltz et al. |
| 6,131,576 A | 10/2000 | Davis |
| 6,158,583 A | 12/2000 | Forster |
| 6,210,419 B1 | 4/2001 | Mayenberger et al. |
| 6,217,590 B1 | 4/2001 | Levinson |

(56) References Cited

U.S. PATENT DOCUMENTS

| | | |
|---|---|---|
| 6,228,104 B1 | 5/2001 | Fogarty et al. |
| 6,258,105 B1 | 7/2001 | Hart et al. |
| 6,261,303 B1 | 7/2001 | Mayenberger et al. |
| 6,273,253 B1 | 8/2001 | Forster et al. |
| 6,273,887 B1 | 8/2001 | Yamauchi et al. |
| 6,273,902 B1 | 8/2001 | Fogarty et al. |
| 6,277,117 B1 | 8/2001 | Tetzlaff et al. |
| 6,349,727 B1 | 2/2002 | Stewart, Jr. |
| 6,352,541 B1 | 3/2002 | Kienzle et al. |
| 6,387,112 B1 | 5/2002 | Fogarty et al. |
| 6,391,035 B1 | 5/2002 | Appleby et al. |
| 6,419,682 B1 | 7/2002 | Appleby et al. |
| 6,537,289 B1 | 3/2003 | Kayan et al. |
| 6,558,408 B1 | 5/2003 | Fogarty et al. |
| 6,599,298 B1 | 7/2003 | Forster et al. |
| 6,695,854 B1 | 2/2004 | Kayan et al. |
| 6,699,258 B1 | 3/2004 | Sadler et al. |
| 6,719,766 B1 | 4/2004 | Buelna et al. |
| 6,773,438 B1 | 8/2004 | Knodel et al. |
| 6,780,195 B2 | 8/2004 | Porat |
| 6,814,742 B2 | 11/2004 | Kimura et al. |
| 6,824,547 B2 | 11/2004 | Wilson et al. |
| 6,837,895 B2 | 1/2005 | Mayenberger |
| 6,843,253 B2 | 1/2005 | Parkes |
| 6,863,675 B2 | 3/2005 | Wilson, Jr. |
| 6,880,699 B2 | 4/2005 | Gallagher |
| 6,926,712 B2 | 8/2005 | Phan |
| 6,932,816 B2 | 8/2005 | Phan |
| 6,989,017 B2 | 1/2006 | Howell et al. |
| 7,001,412 B2 | 2/2006 | Gallagher et al. |
| 7,052,504 B2 | 5/2006 | Hughett |
| 7,094,245 B2 | 8/2006 | Adams et al. |
| 7,108,699 B2 | 9/2006 | Kobayashi |
| 7,131,977 B2 | 11/2006 | Fowler |
| 7,179,265 B2 | 2/2007 | Manetakis et al. |
| 7,211,091 B2 | 5/2007 | Fowler et al. |
| 7,211,092 B2 | 5/2007 | Hughett |
| 7,261,724 B2 | 8/2007 | Molitor et al. |
| 7,316,696 B2 | 1/2008 | Wilson et al. |
| 7,326,223 B2 | 2/2008 | Wilson, Jr. |
| 7,329,266 B2 | 2/2008 | Royse et al. |
| 7,357,805 B2 | 4/2008 | Masuda et al. |
| 7,402,164 B2 | 7/2008 | Watson et al. |
| 7,572,266 B2 | 8/2009 | Young et al. |
| 7,585,304 B2 | 9/2009 | Hughett |
| 7,635,374 B2 | 12/2009 | Monassevitch et al. |
| 7,645,285 B2 | 1/2010 | Cosgrove et al. |
| 7,648,514 B1 | 1/2010 | Nakao |
| 7,727,231 B2 | 6/2010 | Swanson |
| 7,753,908 B2 | 7/2010 | Swanson |
| 7,785,324 B2 | 8/2010 | Eberl |
| 7,963,964 B2 | 6/2011 | Santilli et al. |
| 7,992,757 B2 | 8/2011 | Wheeler et al. |
| 8,137,368 B2 | 3/2012 | Kayan et al. |
| 8,142,451 B2 | 3/2012 | Boulnois et al. |
| 8,262,639 B2 | 9/2012 | Mathias |
| 8,312,992 B2 | 11/2012 | Disch |
| 8,403,138 B2 | 3/2013 | Weisshaupt et al. |
| 8,425,412 B2 | 4/2013 | Rucker |
| 8,465,507 B2 | 6/2013 | Cosgrove et al. |
| 8,512,357 B2 | 8/2013 | Viola |
| 8,585,718 B2 | 11/2013 | Disch et al. |
| 8,764,774 B2 | 7/2014 | Sigmon, Jr. |
| 8,839,954 B2 | 9/2014 | Disch |
| 8,852,216 B2 | 10/2014 | Cropper et al. |
| 8,894,666 B2 | 11/2014 | Schulz et al. |
| 8,900,253 B2 | 12/2014 | Aranyi et al. |
| 8,945,151 B2 | 2/2015 | Salas |
| 8,992,566 B2 | 3/2015 | Baldwin |
| 9,084,596 B2 | 7/2015 | Stanley et al. |
| 9,119,627 B2 | 9/2015 | Cosgrove et al. |
| 9,220,507 B1 | 12/2015 | Patel et al. |
| 9,271,737 B2 | 3/2016 | Castro et al. |
| 9,282,972 B1 | 3/2016 | Patel et al. |
| 9,445,820 B2 | 9/2016 | Whiting |
| 9,456,824 B2 | 10/2016 | Willett et al. |
| 9,498,241 B2 * | 11/2016 | Leonhard ............... A61B 17/29 |
| 9,737,309 B1 | 8/2017 | Ad |
| 9,775,635 B2 | 10/2017 | Takei |
| 9,855,053 B2 | 1/2018 | Bagaoisan et al. |
| 9,901,352 B2 | 2/2018 | Fago et al. |
| 9,955,977 B2 | 5/2018 | Martinez et al. |
| 10,064,623 B2 | 9/2018 | Soutorine et al. |
| 10,136,898 B2 | 11/2018 | Schmidt et al. |
| 10,285,712 B2 | 5/2019 | Cosgrove et al. |
| 10,292,712 B2 | 5/2019 | Shankarsetty |
| 10,307,166 B2 | 6/2019 | Willett et al. |
| 10,383,637 B2 | 8/2019 | Castro |
| 10,548,609 B2 | 2/2020 | Ramsey et al. |
| 10,758,243 B2 | 9/2020 | Salas |
| 10,925,616 B2 | 2/2021 | Shellenberger et al. |
| 11,160,550 B2 | 11/2021 | Harris et al. |
| 11,160,559 B2 | 11/2021 | Shellenberger |
| 11,266,408 B2 | 3/2022 | Shellenberger |
| 11,534,177 B2 | 12/2022 | Shellenberger et al. |
| 11,576,680 B2 | 2/2023 | Ramsey et al. |
| 11,607,227 B2 | 3/2023 | Shellenberger |
| 11,883,034 B2 | 1/2024 | Enniss |
| 2002/0046961 A1 | 4/2002 | Levinson et al. |
| 2002/0068946 A1 | 6/2002 | Kortenbach et al. |
| 2002/0111640 A1 | 8/2002 | Krause et al. |
| 2002/0169459 A1 | 11/2002 | Porat |
| 2003/0014060 A1 | 1/2003 | Wilson et al. |
| 2003/0074009 A1 | 4/2003 | Ramsey et al. |
| 2003/0158548 A1 | 8/2003 | Phan et al. |
| 2004/0010272 A1 | 1/2004 | Manetakis et al. |
| 2004/0040875 A1 | 3/2004 | Gallagher |
| 2004/0044352 A1 | 3/2004 | Fowler et al. |
| 2004/0059359 A1 | 3/2004 | Wilson |
| 2004/0097970 A1 | 5/2004 | Hughett |
| 2004/0172043 A1 | 9/2004 | Watson et al. |
| 2005/0090838 A1 | 4/2005 | Sixto et al. |
| 2005/0149063 A1 | 7/2005 | Young et al. |
| 2005/0149068 A1 | 7/2005 | Williams et al. |
| 2005/0149069 A1 | 7/2005 | Bertolero et al. |
| 2005/0165421 A1 | 7/2005 | Wilson et al. |
| 2005/0165422 A1 | 7/2005 | Wilson, Jr. |
| 2005/0165423 A1 | 7/2005 | Gallagher et al. |
| 2005/0165429 A1 | 7/2005 | Douglas et al. |
| 2005/0171560 A1 | 8/2005 | Hughett |
| 2005/0234478 A1 | 10/2005 | Wixey et al. |
| 2005/0240219 A1 | 10/2005 | Kahle et al. |
| 2005/0277959 A1 * | 12/2005 | Cosgrove ............. A61B 17/122 606/151 |
| 2006/0124485 A1 | 6/2006 | Kennedy |
| 2006/0217749 A1 | 9/2006 | Wilson et al. |
| 2007/0016228 A1 | 1/2007 | Salas |
| 2007/0049947 A1 | 3/2007 | Menn et al. |
| 2007/0083218 A1 | 4/2007 | Steven |
| 2007/0118161 A1 | 5/2007 | Kennedy et al. |
| 2007/0149989 A1 | 6/2007 | Santilli et al. |
| 2007/0276417 A1 | 11/2007 | Mendes et al. |
| 2007/0282355 A1 | 12/2007 | Brown et al. |
| 2008/0287976 A1 | 11/2008 | Weaner et al. |
| 2008/0312670 A1 | 12/2008 | Lutze et al. |
| 2009/0012545 A1 | 1/2009 | Williamson et al. |
| 2009/0088783 A1 | 4/2009 | Kennedy et al. |
| 2009/0088786 A1 | 4/2009 | Zook et al. |
| 2009/0112233 A1 | 4/2009 | Xiao |
| 2009/0171380 A1 | 7/2009 | Whiting |
| 2009/0240266 A1 | 9/2009 | Dennis |
| 2010/0057107 A1 | 3/2010 | Sorrentino et al. |
| 2010/0082047 A1 | 4/2010 | Cosgrove et al. |
| 2010/0114131 A1 | 5/2010 | Rotunda |
| 2010/0211080 A1 | 8/2010 | Trivisani et al. |
| 2010/0274262 A1 | 10/2010 | Schulz et al. |
| 2010/0274264 A1 | 10/2010 | Schulz et al. |
| 2010/0274268 A1 | 10/2010 | Singh et al. |
| 2011/0022079 A1 | 1/2011 | Miles et al. |
| 2011/0087244 A1 | 4/2011 | Weisshaupt et al. |
| 2011/0144665 A1 | 6/2011 | Malkowski |
| 2011/0245848 A1 | 10/2011 | Rosenberg et al. |
| 2011/0295291 A1 | 12/2011 | Trivisani |
| 2012/0074200 A1 | 3/2012 | Schmid et al. |

(56) References Cited

U.S. PATENT DOCUMENTS

| | | |
|---|---|---|
| 2012/0083803 A1 | 4/2012 | Patel et al. |
| 2012/0226291 A1 | 9/2012 | Malizia et al. |
| 2012/0277765 A1 | 11/2012 | Zammataro et al. |
| 2012/0330326 A1 | 12/2012 | Creston et al. |
| 2013/0006271 A1 | 1/2013 | Vold et al. |
| 2013/0226200 A1 | 8/2013 | Kappel et al. |
| 2013/0245651 A1 | 9/2013 | Schmidt et al. |
| 2013/0245652 A1 | 9/2013 | Cosgrove et al. |
| 2013/0253535 A1 | 9/2013 | Pribanic et al. |
| 2013/0261642 A1 | 10/2013 | Willett et al. |
| 2014/0018830 A1 | 1/2014 | Shelton, IV |
| 2014/0058411 A1 | 2/2014 | Soutorine et al. |
| 2014/0207156 A1 | 7/2014 | Malkowski |
| 2014/0243862 A1 | 8/2014 | Bagaoisan et al. |
| 2014/0309677 A1 | 10/2014 | Baldwin |
| 2014/0367447 A1* | 12/2014 | Woodard, Jr. ... A61B 17/00234 227/176.1 |
| 2015/0066057 A1 | 3/2015 | Malkowski et al. |
| 2015/0105821 A1* | 4/2015 | Ward ................ A61B 17/29 606/206 |
| 2015/0136835 A1 | 5/2015 | Shelton et al. |
| 2015/0190137 A1 | 7/2015 | Salas |
| 2015/0320426 A1 | 11/2015 | Cosgrove et al. |
| 2016/0151073 A1 | 6/2016 | Castro et al. |
| 2016/0174981 A1 | 6/2016 | Fago et al. |
| 2016/0213377 A1 | 7/2016 | Shankarsetty |
| 2016/0242773 A1* | 8/2016 | Sadowski ............ A61B 17/105 |
| 2016/0256157 A1 | 9/2016 | Rockrohr et al. |
| 2016/0270790 A1 | 9/2016 | Jankowski |
| 2016/0354089 A1 | 12/2016 | Whiting |
| 2017/0014135 A1 | 1/2017 | Martin et al. |
| 2017/0238935 A1 | 8/2017 | Shi |
| 2017/0252042 A1 | 9/2017 | Kethman et al. |
| 2018/0036008 A1 | 2/2018 | Ramsey et al. |
| 2018/0168659 A1 | 6/2018 | Bagaoisan et al. |
| 2018/0271527 A1 | 9/2018 | Shellenberger |
| 2018/0271532 A1 | 9/2018 | Shellenberger |
| 2018/0271534 A1 | 9/2018 | Shellenberger |
| 2018/0271535 A1 | 9/2018 | Shellenberger et al. |
| 2018/0271536 A1 | 9/2018 | Shellenberger et al. |
| 2019/0321048 A1* | 10/2019 | Dinino ............... A61B 17/1285 |
| 2021/0128159 A1 | 5/2021 | Taylor et al. |
| 2022/0047271 A1 | 2/2022 | Shellenberger |

FOREIGN PATENT DOCUMENTS

| | | |
|---|---|---|
| CN | 1846638 A | 10/2006 |
| CN | 101543418 A | 9/2009 |
| CN | 103181809 A | 7/2013 |
| CN | 103442658 A | 12/2013 |
| CN | 103930054 A | 7/2014 |
| CN | 104039248 A | 9/2014 |
| CN | 104367363 A | 2/2015 |
| CN | 104414701 A | 3/2015 |
| CN | 105054989 A | 11/2015 |
| CN | 105078536 A | 11/2015 |
| CN | 105816217 A | 8/2016 |
| CN | 106037947 A | 10/2016 |
| CN | 106264646 A | 1/2017 |
| CN | 110740696 A | 1/2020 |
| EP | 0086640 A2 | 8/1983 |
| EP | 0201344 A2 | 11/1986 |
| EP | 0314064 A2 | 5/1989 |
| EP | 0576835 A2 | 1/1994 |
| EP | 1233705 A2 | 8/2002 |
| EP | 0893969 B1 | 6/2005 |
| EP | 2074954 A1 | 7/2009 |
| EP | 2502578 A1 | 9/2012 |
| EP | 3493747 A1 | 6/2019 |
| EP | 3600084 A1 | 2/2020 |
| GB | 2054027 A | 2/1981 |
| GB | 2069848 A | 9/1981 |
| GB | 2353710 A | 3/2001 |
| GB | 2465560 A | 5/2010 |
| JP | 56-151034 A | 11/1981 |
| JP | 61-007818 B2 | 3/1986 |
| JP | 61-259652 A | 11/1986 |
| JP | 03-178648 A | 8/1991 |
| JP | 05-200039 A | 8/1993 |
| JP | 2002-345828 A | 12/2002 |
| JP | 2004-522468 A | 7/2004 |
| JP | 2004-535236 A | 11/2004 |
| JP | 4263594 B2 | 5/2009 |
| JP | 2011-036675 A | 2/2011 |
| JP | 2011-517423 A | 6/2011 |
| JP | 2014-531250 A | 11/2014 |
| JP | 2015-043977 A | 3/2015 |
| JP | 7329038 B2 | 8/2023 |
| WO | 97/38634 A1 | 10/1997 |
| WO | 01/35837 A1 | 5/2001 |
| WO | 01/37742 A2 | 5/2001 |
| WO | 2004/043225 A2 | 5/2004 |
| WO | 2005/107613 A1 | 11/2005 |
| WO | 2006/102578 A1 | 9/2006 |
| WO | 2012/075532 A1 | 6/2012 |
| WO | 2013/040467 A2 | 3/2013 |
| WO | 2015/099067 A1 | 7/2015 |
| WO | 2016/081822 A1 | 5/2016 |
| WO | 2016/094647 A1 | 6/2016 |
| WO | 2018/027032 A1 | 2/2018 |
| WO | 2018/175626 A1 | 9/2018 |
| WO | 2020/018784 A1 | 1/2020 |

* cited by examiner

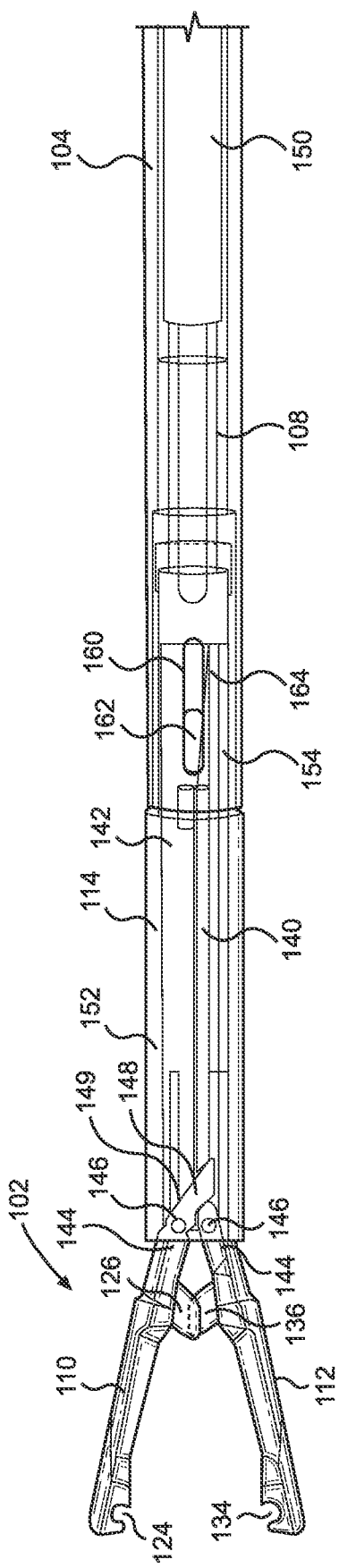
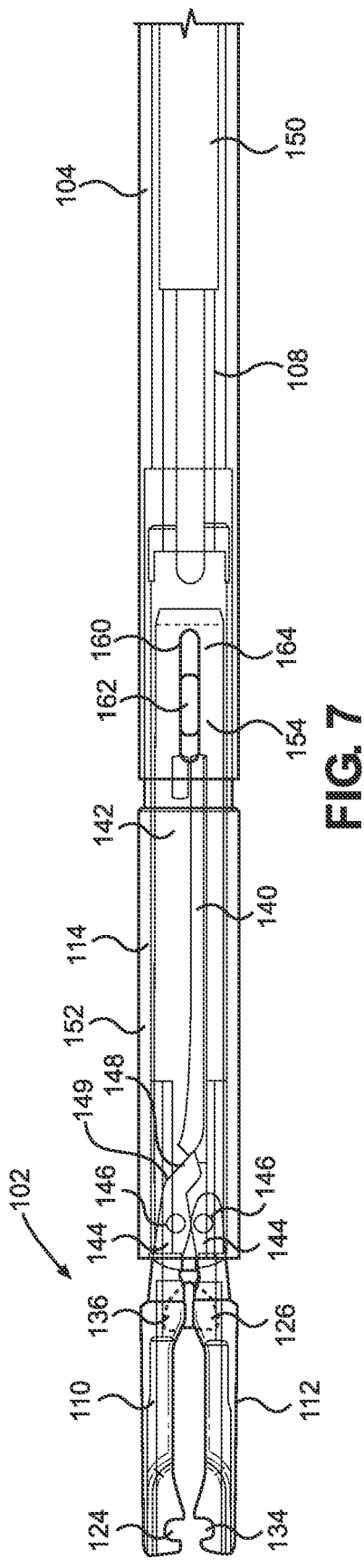
FIG. 6
FIG. 7

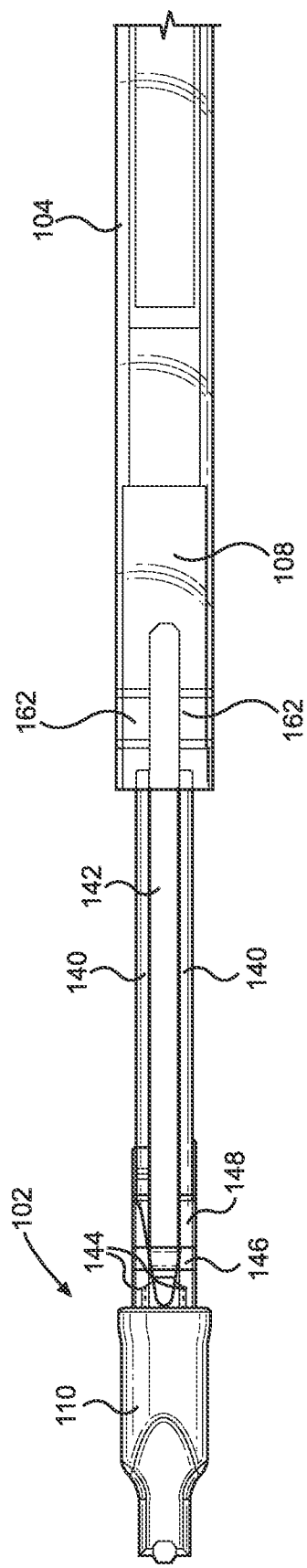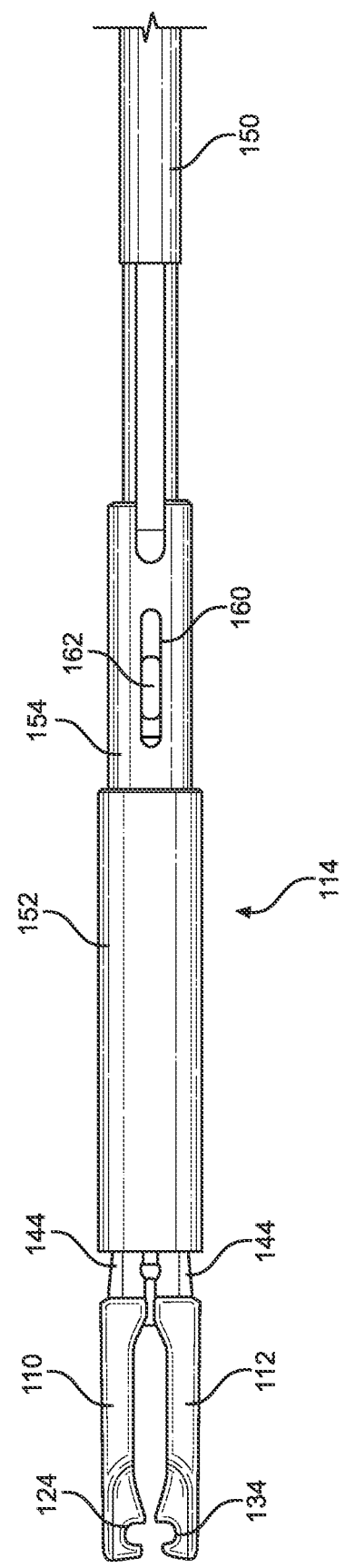

CLIP APPLIER

PRIORITY

This application is a continuation of International Patent Application PCT/US2020/052746 (filed Sep. 25, 2020), which claims the benefit of priority of U.S. Provisional Patent Application No. 62/906,585 (filed Sep. 26, 2019), the disclosures of which are expressly incorporated herein by reference in their entirety.

TECHNICAL FIELD

The present disclosure relates generally to clip appliers, and more particularly, to clip appliers with improved actuation mechanisms and/or stabilizing members configured to stabilize a surgical clip.

BACKGROUND

Ligation of tissue (e.g., blood vessels, lymph nodes, nerves, fallopian tubes, and cardiac tissue) is a common practice for many surgical procedures. This can be performed by closing the vessel with a surgical clip or by suturing the vessel with the surgical thread. The use of surgical thread requires complex manipulations of a needle and surgical thread to form knots required to secure the vessel. Such complex manipulations are time consuming and difficult to perform, particularly in endoscopic surgical procedures characterized by limited space and/or visibility. In contrast, surgical clips are relatively quick and easy to apply. Accordingly, the use of surgical clips in endoscopic and open surgical procedures has grown dramatically.

SUMMARY

The present inventor recognizes that there is a need to improve one or more features of the clip appliers, such as stability of the surgical clip in a clip applier and/or ease of actuation. Surgical clips are often applied by clip appliers with a pair of opposing jaws. Currently available clip appliers often secure the clip with two points of contact, for example, the opposing jaws may engage bosses on distal ends of the surgical clip. However, the two points of contact do not provide sufficient stability to the surgical clip, which may cause the surgical clip to become misaligned relative to the clip applier during a surgical procedure, or even fall out. Furthermore, current clip appliers often do not provide sufficient closing force and/or reliable opening of the jaws. The disclosed methods and systems are directed to mitigating or overcoming one or more of the problems set forth above and/or other problems in the prior art.

A first aspect of the present invention is directed to a clip applier configured to apply a surgical clip. The clip applier may include a first jaw member and a second jaw member. The first jaw member may include a first inner surface and a first stabilizing member extending from the first inner surface, and may be configured to engage a distal portion of a first leg member of the surgical clip. The second jaw member may include a second inner surface and a second stabilizing member extending from the second inner surface. The second jaw member may be configured to engage a distal portion of a second leg member of the surgical clip. The first stabilizing member and the second stabilizing member may be configured to be positioned on opposite lateral sides of a proximal portion of the surgical clip to reduce lateral movement of the surgical clip.

A second aspect of the present invention is directed to an assembly including a surgical clip having a first leg member and a second leg member, and a clip applier. The clip applier may include a first jaw member and a second jaw member. The first jaw member may include a first inner surface and a first stabilizing member extending from the first inner surface, and may be configured to engage a distal portion of the first leg member of the surgical clip. The second jaw member may include a second inner surface and a second stabilizing member extending from the second inner surface. The second jaw member may be configured to engage a distal portion of the second leg member of the surgical clip. The first stabilizing member and the second stabilizing member may be configured to be positioned on opposite lateral sides of a proximal portion of the surgical clip to reduce lateral movement of the surgical clip.

In some embodiments, an inner portion of the first stabilizing member is spaced apart from the second jaw member in an open configuration, and an inner portion of the second stabilizing member is spaced apart from the first jaw member in the open configuration. In some embodiments, the first jaw member has a first channel in the first inner surface, and the second jaw member has a second channel in the second inner surface, where the first channel does not receive the second stabilizing member in the open configuration, the first channel receives the second stabilizing member in a closed configuration, the second channel does not receive the first stabilizing member in the open configuration, and the second channel receives the first stabilizing member in the closed configuration. In some embodiments, the first channel has a widened proximal portion configured to receive the second stabilizing member, and the second channel has a widened proximal portion configured to receive the first stabilizing member. In some embodiments, the first stabilizing member includes a first wall extending longitudinally along the first inner surface, the second stabilizing member includes a second wall longitudinally extending along the second inner surface, and the first wall and the second wall are disposed on opposite lateral sides of a longitudinal axis of the clip applier. In some embodiments, each of the first stabilizing member and the second stabilizing member has at least one substantially flat lateral surface. In some embodiments, the first stabilizing member and the second stabilizing member extend substantially parallel in the open configuration and the closed configuration. In some embodiments, the first stabilizing member and the second stabilizing member laterally overlap in the closed configuration. In some embodiments, the first stabilizing member and the second stabilizing member do not laterally overlap in the open configuration. In some embodiments, each of the first stabilizing member and the second stabilizing member has an inner portion defining an apex extending distally in the open configuration. In some embodiments, the first inner surface has at least one first recess on a distal portion configured to receive a first boss on the first leg member of the surgical clip, and the second inner surface has at least one second recess on a distal portion configured to receive a second boss on the second leg member of the surgical clip. In some embodiments, the first stabilizing member is integral to the first jaw member, and the second stabilizing member is integral to the second jaw member. In some embodiments, the first stabilizing member and the second stabilizing member are configured to not proximally contact a proximal end of the surgical clip in the open configuration.

A third aspect of the invention is directed to a clip applier configured to apply a surgical clip. The clip applier may include a first jaw member and a second jaw member, where the first jaw member is configured to pivot between an open configuration and a closed configuration. The clip applier may also include a leaf spring configured to bias the first jaw member into the open configuration, and a tubular member configured to advance over the first jaw member to cam the first jaw member into a closed configuration against the bias of the leaf spring.

In some embodiments, the clip applier has a second leaf spring configured to bias the second jaw member into an open configuration, where the second jaw member is configured to pivot between the open configuration and the closed configuration, and the tubular member is configured to advance over the second jaw member to cam the second jaw member into the closed configuration against the bias of the second leaf spring. In some embodiments, the leaf spring overlaps with a proximal portion of the first jaw member to bias the first jaw member into the open configuration, and the second leaf spring overlaps with a proximal portion of the second jaw member to bias the second jaw member into the open configuration. In some embodiments, the proximal portion of each of the first and second jaw members includes a proximal extension angled relative to a longitudinal axis of the clip applier. In some embodiments, the proximal extension extends from only one lateral side of the respective first and second jaw member. In some embodiments, the first jaw member and the second jaw member each has a proximal portion and a distal portion, the proximal portion having a width less than the distal portion and configured to be received in the tubular member. In some embodiments, the clip applier has a connector disposed in the tubular member, where the leaf spring and the second leaf spring are disposed on opposite lateral sides of the connector. In some embodiments, a proximal portion of the leaf spring and a proximal portion of the second leaf spring are fixed to the connector. In some embodiments, at least one of the first jaw member and the second jaw member is pivotably coupled to the connector. In some embodiments, the first jaw member is pivotably coupled to the connector at a first pivot pin, and the second jaw member is pivotably coupled to the connector at a second pivot pin. In some embodiments, the proximal portion of at least one of the first jaw member and the second jaw member straddles a distal portion of the connector. In some embodiments, the tubular member includes a distal portion and a proximal portion, the distal portion having a larger diameter than the proximal portion, where the distal portion is configured to cam the first jaw member and second jaw member into the closed configuration. In some embodiments, the connector has a pin, the tubular member has an elongated slot, where the pin travels through the elongated slot as the tubular member advances. In some embodiments, the pin of the connector is fixed to a shaft receiving the tubular member. In some embodiments, the clip applier includes a shaft, a handle assembly on a proximal end of the shaft, and an actuator extending through the shaft and actuated by the handle assembly, where the actuator is configured to advance through the shaft to advance the tubular member over the first jaw member and the second jaw member.

BRIEF DESCRIPTION OF THE DRAWINGS

In order that the disclosure may be readily understood, aspects of this disclosure are illustrated by way of examples in the accompanying drawings.

FIG. 6 illustrates a side view of the clip applier of FIGS. 1-5 in an open configuration.

FIG. 7 illustrates a side view of the clip applier of FIGS. 1-6 in a closed configuration.

FIG. 8 illustrates a top view of the clip applier of FIGS. 1-7 in the closed configuration with an overtube removed.

FIG. 9 illustrates a side view of the clip applier of FIGS. 1-8 in the closed configuration with a shaft removed.

The same or similar reference numbers are used in the drawings and the following detailed description to refer to the same or similar parts.

DETAILED DESCRIPTION

Figure 1:
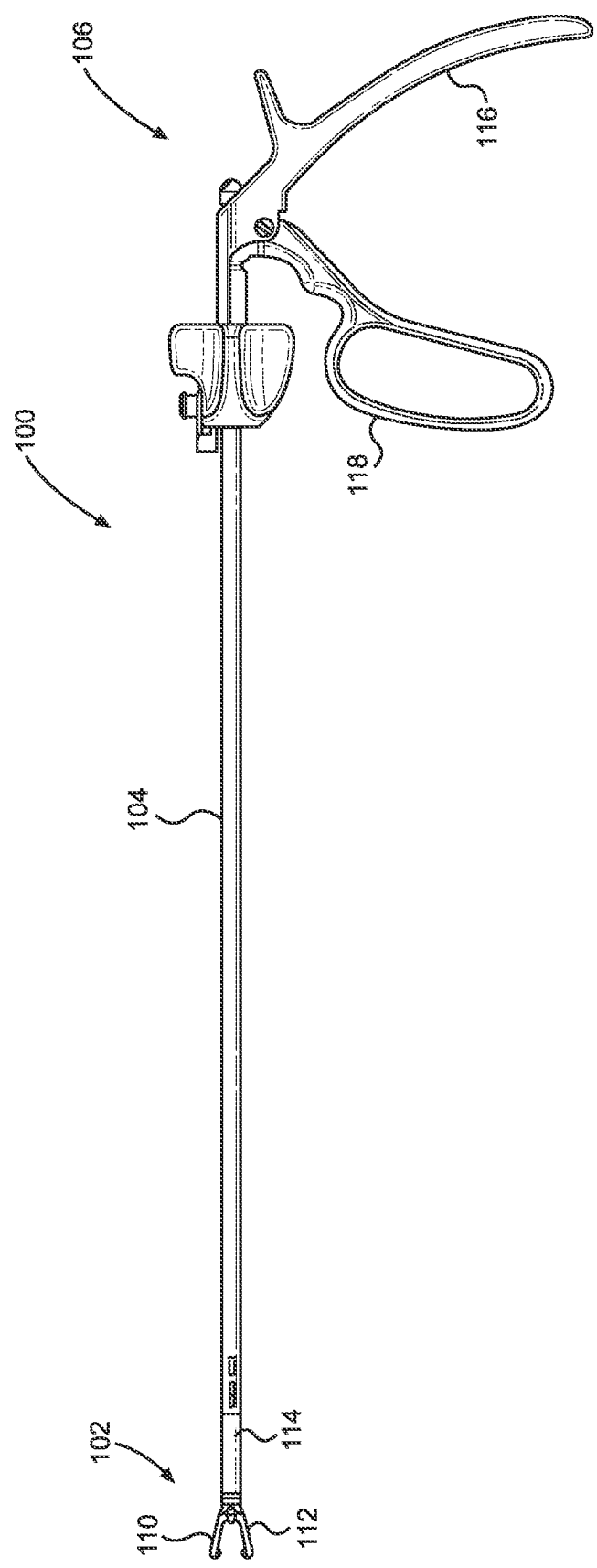
FIG. 1 illustrates an exemplary embodiment of a clip applier of the present disclosure.

The invention will now be described with reference to the figures, in which like reference numerals refer to like parts throughout. In accordance with conventional practice, as used herein, and unless otherwise indicated herein, the term "proximal" refers to the relative positioning of a clip applier or component generally closer to a user or medical personnel handling or manipulating the device as it is intended to be used, and the term "distal" refers to the relative positioning of the clip applier or component further from the user or medical personnel handling or manipulating the device as it is intended to be used. The term "vertical" refers to a relative direction of the clip applier parallel or along a plane extending evenly through both jaw members or similarly to the component. The term "longitudinal" refers to a relative direction along a long axis or length of the clip applier or component. The term "lateral" refers to a relative direction parallel to or along a plane extending perpendicularly between the first and second jaw members or similarly to the component.

FIG. 1 illustrates an exemplary clip applier 100 having a jaw assembly 102, a shaft 104, and a handle assembly 106. The jaw assembly 102 may include a first jaw member 110 and a second jaw member 112 pivotably coupled at a distal portion of the shaft 104 and actuatable by longitudinal movement of an overtube or tubular member 114. Movement of the tubular member 114 may be caused by relative movement of a first handle member 116 and a second handle member 118. For example, the first handle member 116 may be fixed and the second handle member 118 may be pivotably moveable at a pivot pin, such that pivoting of the second handle member 118 relative to the first handle member 116 may cause longitudinal advancement of the tubular member 114. The tubular member 114 may include camming surfaces at the distal end of the tubular member 114 that cam the first and second jaw members 110, 112 into a closed configuration. The clip applier 100 may be a manual clip applier, which a user or medical personnel front-loads surgical clips 50 individually into the jaw assembly 102 from a clip cartridge (not shown) and applies each of the surgical clips 50 individually to tissue after each loading. Further disclosure of the manual loading of the clip applier 100 may be found in U.S. Pat. No. 6,880,699, the entire disclosure of which is incorporated herein by reference in its entirety.

Figure 2:
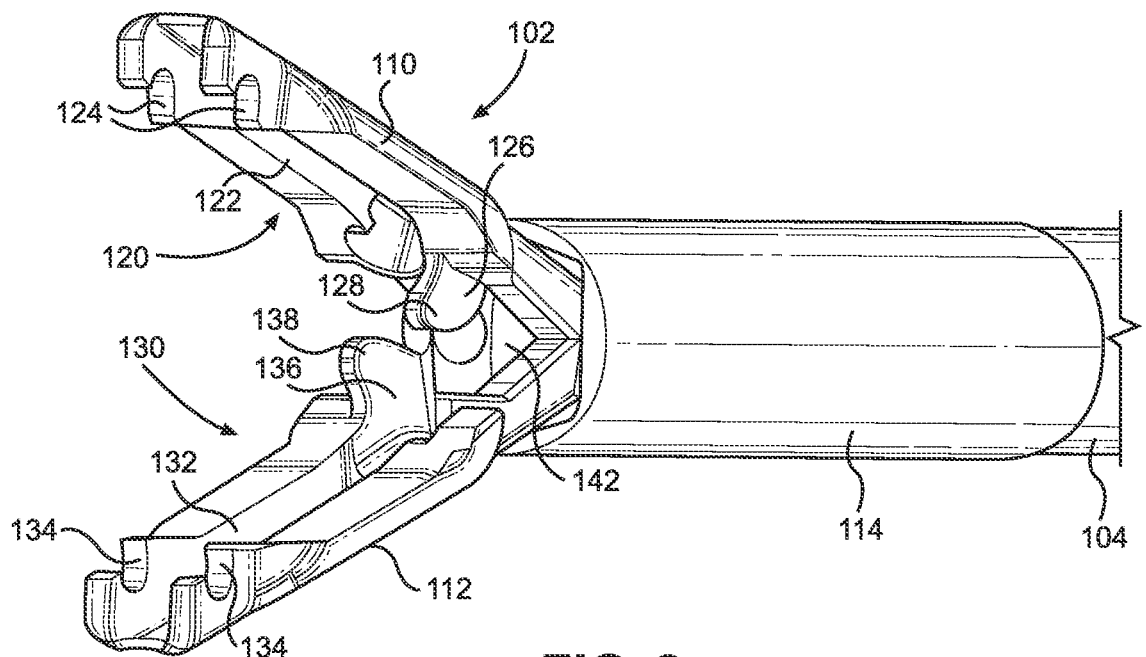
FIG. 2 illustrates a perspective view of a distal end effector of the clip applier of FIG. 1.
Figure 3:
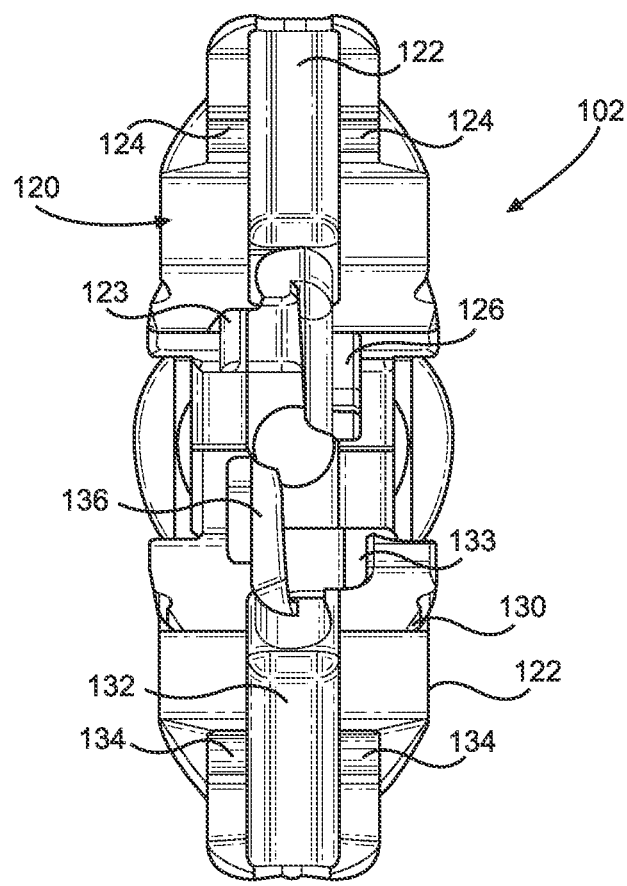
FIG. 3 illustrates a frontal view of the distal end effector of FIG. 2.
Figure 4:
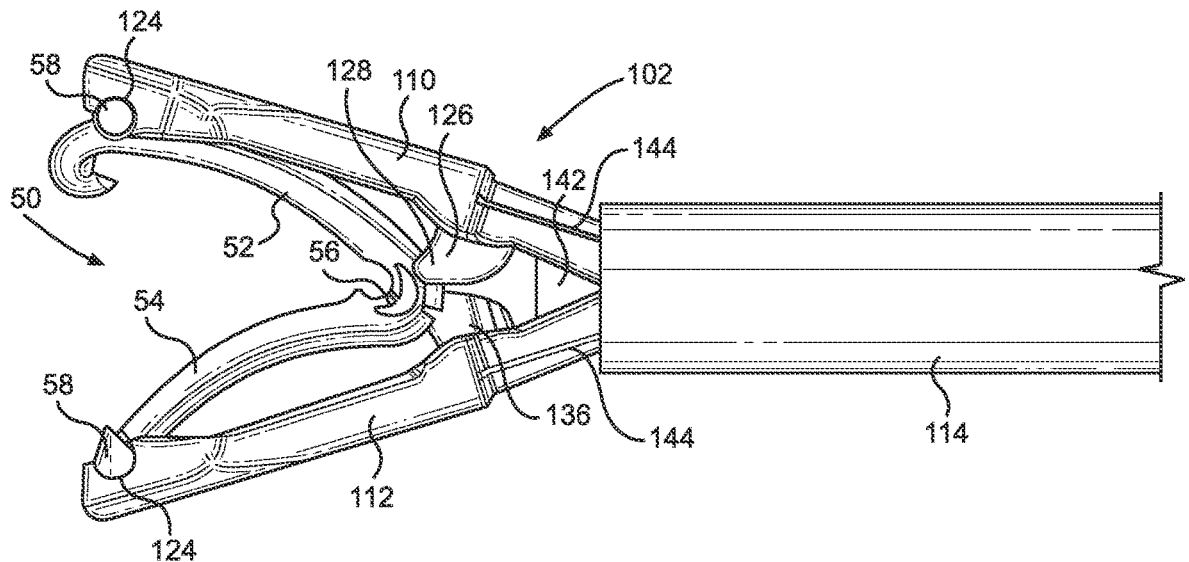
FIG. 4 illustrates a side view of the distal end effector of FIGS. 2-3 loaded with an exemplary surgical clip.
Figure 5:
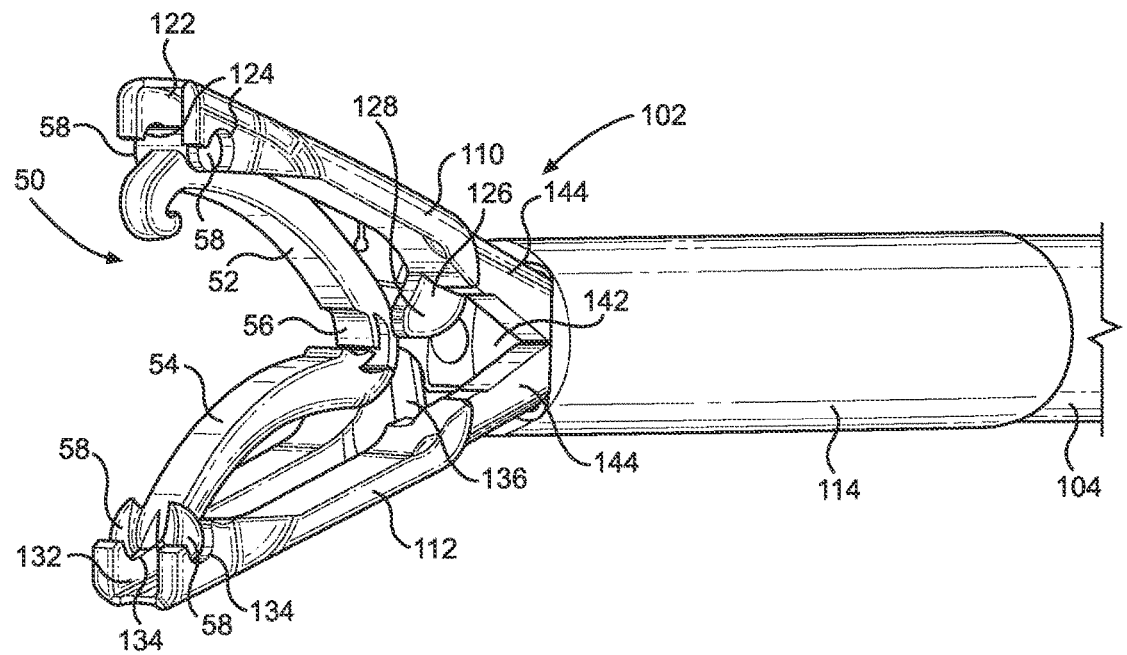
FIG. 5 illustrates a perspective view of the distal end effector of FIGS. 2-4 loaded with the exemplary surgical clip.

FIG. 2 illustrates a first perspective view of an exemplary embodiment of the jaw assembly 102 of the clip applier 100, and FIG. 3 illustrates a frontal view of the jaw assembly 102. FIG. 4 illustrates a side view of the jaw assembly 102 loaded with a surgical clip 50, and FIG. 5 illustrates a perspective view of the jaw assembly 102 loaded with the surgical clip 50. FIG. 6 illustrates a side view of the clip applier 100 in an open configuration, and FIG. 7 illustrates a side view of the clip applier 100 in the closed configuration. FIG. 8 illustrates atop view of the clip applier 100 in the closed configuration with the tubular member 114 removed for clarity purposes. FIG. 9 illustrates a side view of the clip applier 100 in the closed configuration with the shaft 104 removed for clarity purposes.

As illustrated in FIGS. 2-3, the first jaw member 110 may include a first inner surface 120 having a first longitudinal channel 122, one or more recesses 124 on a distal portion, and a stabilizing member 126 on a proximal portion. The second jaw member 112 may include a second inner surface 130 having a second longitudinal channel 132, one or more recesses 134 on a distal portion, and a stabilizing member 136 on a proximal portion. The recesses 124, 134 may be substantially semi-circular grooves at the distal portions of the jaw members 110, 112. The stabilizing members 126, 136 may be integral to the respective jaw member 110, 112. The stabilizing members 126, 136 may be substantially rigid and extend substantially parallel to a longitudinal axis of the jaw members 110, 112 in the open and closed configurations, and create a longitudinal space therebetween. The first stabilizing member 126 may include a first wall projecting from the first inner surface 120 and extending longitudinally along the first inner surface 120, the second stabilizing member 136 may include a second wall projecting from the second inner surface 130 and extending along the second inner surface 130. The first and second walls 126, 136 may be fin shaped, including a concave and/or angled distal surface and a convex and/or angled proximal surface, each relative to the inner surface 120, 130 to define a distally-facing apex at an inner portion 128, 138. The inner portion 128, 138 may extend distally in the open configuration, as illustrated in FIG. 4. The first and second jaw members 110, 112 may be rotationally symmetric, such that the first and second stabilizing members 126, 136 may be disposed on opposite lateral sides of a longitudinal axis of the clip applier. The surgical clip 50 may be received along the longitudinal axis of the clip applier, thus the stabilizing members 126, 136 may be positioned on opposite sides of a proximal portion of the surgical clip 50.

The stabilizing members 126, 136 may or may not laterally overlap each other in the open configuration (e.g., FIGS. 1-6), and the stabilizing members 126, 136 may laterally overlap each other in the closed configuration (e.g., FIG. 7). The first inner portion 128 may be spaced apart from the second jaw member 112 and not be received in the second longitudinal channel 132 in the open configuration (e.g., FIGS. 2-6). The first inner portion 128 may be received in the second longitudinal channel 132 in the closed configuration (e.g., FIG. 7). Similarly, the second inner portion 138 may be spaced apart from the first jaw member 110 and not be received in the first longitudinal channel 122 in the open configuration (e.g., FIG. 2-6). The second inner portion 138 may be received in the first longitudinal channel 122 in the closed configuration, and the second inner portion 138 may be received in the first longitudinal channel 122 in the closed configuration (e.g., FIG. 7). For example, as further illustrated in FIG. 3, the first longitudinal channel 122 may include a widened proximal portion 123 configured to receive the second stabilizing member 136, and the second longitudinal channel 132 may include a widened proximal portion 133 to receive the first stabilizing member 126. The widened proximal portions 123, 133 may be lateral, off-axis relative to the longitudinal axis of the clip applier 100, such that the longitudinal channels are asymmetric relative to the longitudinal axis. The stabilizing members 126, 136 may each include at least one lateral flat surface to facilitate insertion into the respective longitudinal channel 122, 132 and/or provide lateral stability of the surgical clip 50. For example, the stabilizing members 126, 136 may each include a flat laterally exterior surface to slide along a flat interior side surface of the widened proximal portions 123, 133. The first longitudinal channel 122 and/or second longitudinal channel 132 may also receive a portion of the surgical 50 in the open configuration (as illustrated in FIG. 4) and/or closed configuration.

As illustrated in FIGS. 4-5, the jaw assembly 102 may be configured to hold the surgical clip 50 with at least three points of contact. The surgical clip 50 may include a first leg member 52 and a second leg member 54 having proximal ends pivotably joined at a hinge portion 56. The surgical clip 50 may include one or more bosses 58 at a distal portion of each of the first and second leg members 52, 54. The bosses 58 may be circular corresponding to the recesses 124, 134 and be releasably received in the recesses 124, 134 to secure the distal portion of the surgical clip 50. Furthermore, the proximal portion of the surgical clip 50 (e.g., the hinge portion 56) may be received between the stabilizing members 126, 136 to reduce lateral movement or fish-tailing of the surgical clip 50. Each of the inner portions (e.g., distally-facing apex) 128, 138 of the stabilizing members 126, 136 may laterally overlap with the hinge portion 56 (as illustrated in FIG. 4) to reduce lateral movement or fish-tailing of the surgical clip 50. The first leg member 52 of the surgical clip 50 may have a concave inner surface, a convex outer surface, and a hook member on a distal portion. The second leg member 54 may include convex inner surface, a concave inner surface, and a tip member on a distal portion. As the surgical clip 50 closes, the hook on the first leg member 52 may deflect around the tip member on the second leg member to secure the surgical clip 50 in a latched configuration. Due to the curvatures, the first and/or second leg members 52, 54 may straighten and/or elongate during the closing and/or latching process. The clip applier 100 and/or the stabilizing members 126, 136 may not proximally abut the surgical clip 50 to allow the surgical clip to straighten and/or elongate during the closing and/or latching process.

The surgical clip 50 may be made of any suitable size and may be applied to any number of tissues, such as blood vessels, lymph nodes, nerves, fallopian tubes, or cardiac tissue. The surgical clip 50 may be constructed from any suitable biocompatible material, such as metals and polymers. In some embodiments, the surgical clip 50 consists of a one-piece integral polymeric body formed from a suitable strong biocompatible engineering plastic such as the type commonly used for surgical implants. Exemplary materials include homopolymer or co-polymer polyacetal, polyethylene terephthalate (PET), polybutylene terephthalate (PBT), polyoxymethylene, or other thermoplastic materials having similar properties that can be injection-molded, extruded, or otherwise processed into like articles. Exemplary embodiments and features of the surgical clip 50 are further disclosed in U.S. Pat. No. 4,834,096, the disclosure of which is incorporated herein by reference in its entirety.

As illustrated in FIGS. 6-9, the pivoting of the jaw assembly 102 may be biased into the open configuration by at least one leaf spring 140 and actuated by longitudinal movement of the tubular member 114. The at least one leaf spring 140 may have a distal end that overlaps with at least one of the jaw members 110, 112. For example, the at least one leaf spring 140 may include a pair leaf springs 140 on opposing lateral sides of a vertical beam or connector 142, and a proximal end of the leaf springs 140 may be fixed (e.g., welded) to the connector 142 in a cantilever configuration. The leaf springs 140 may be on opposite vertical sides of the longitudinal axis of the clip applier 100. The jaw members 110, 112 may each have a proximal portion including a pair of proximal members 144. The proximal members 144 of each jaw member 110, 112 may include a pair of legs that are separated from each other and straddle a distal portion of the connector 142 for pivoting stability. The proximal members 144 may be pivotably secured to the connector 142 with at least one pivot pin 146. Thus, the first jaw member 110 may be secured to the connector 142 with at least one first pivot pin 146, and the second jaw member 112 may be secured to the connector 142 with at least one second pivot pin 146. The first and second pivot pins 146 of the jaw members 110, 112 may be on opposing vertical sides of the longitudinal axis of the connector 142. The connector 142 may be fixedly secured in a lumen 108 of the shaft 104 and extend distally out of the tubular member 114. The proximal members 144 may have a width less than a distal length of the jaw members 110, 112, such that the proximal members 144 fit inside the tubular member 144 to be cammed into a closed configuration. The tubular member 144 further prevents the jaw members 110, 112 from flexing in the closed configuration.

One of the proximal members 144 of each of the jaw members 110, 112 may further include a proximal extension 148 proximal of the pivot pin 146 and angled relative to the longitudinal axis of the clip applier 100. The proximal extensions 148 may be leg extensions extending from one proximal member 144 further proximally than the opposing proximal member 144 of the same jaw member 110, 112. The proximal extensions 148 of the first and second jaw members 110, 112 may laterally cross each other at the longitudinal axis of the clip applier 100. Only one of the proximal members 144 of each jaw member 110, 112 may have a proximal extension 148 to enable pivoting by the respective leaf spring 140 and preventing interference by the opposing jaw member 110, 112. The proximal extension 148 may extend from only one lateral side of the respective first and second jaw member 110, 112. Thus, the proximal extensions 148 of the jaw members 110, 112 may extend on opposing lateral sides of the connector 142. The proximal extensions 148 may include an upper surface 149 angled relative to the longitudinal axis. The leaf springs 140 may overlap with or symmetrically lay radially on top of the angled surface of each of the proximal extension 148 of the jaw members 110, 112 in both of the open configuration (FIG. 6) and closed configuration (FIG. 7) to bias the jaw assembly 102 in the open configuration. Thus, the leaf springs 140 may not be deflected (straight) or slightly deflected in the open configuration and be deflected or further deflected in the closed configuration due to the relative angle of the jaw members 110, 112. The deflection of the leaf springs 140 may symmetrically push the extensions 148 of each of the jaw members 110, 112 in opposite directions with respect to the longitudinal axis of the clip applier 100, to bias the jaw assembly 102 into the open configuration. The jaw members 110, 112 may contact each other (e.g., at the proximal extensions 148, as illustrated in FIG. 6) to prevent further pivoting and to provide a stop in the open configuration.

The tubular member 114 may be actuated by longitudinal movement of an actuator 150. The actuator 150 may be an actuating shaft extending through the lumen 108 of the shaft 104 and connected to the handle assembly 106. Squeezing or compressing of the second handle member 118 relative to the first handle member 116 may cause longitudinal advancement of the actuator 150 that causes longitudinal advancement of the tubular member 114 to cam the proximal members 144 of the jaw assembly 102 into the closed configuration against the bias of the leaf springs 140. Release of the second handle member 118 may release the distal force applied to the tubular member 114, such that the bias of the leaf springs 140 may open the jaw members 110, 112 to longitudinally retract the tubular member 114. The tubular member 114 may have a distal portion 152 and a proximal portion 154, where the distal portion 152 has a larger diameter than the proximal portion 154. The distal portion 152 may extend distally of the shaft 104 and may have a diameter that is substantially the same as the diameter of the shaft 104. Thus, the proximal end of the distal portion 152 may abut the distal portion of the shaft 104 when the jaw assembly 102 are in an open configuration (as illustrated in FIG. 6). The distal portion 152 may be configured to receive the proximal portions 144 and to cam the first and second jaw members 110, 112 to close the jaw assembly 102. Thus, the leaf springs 140 may bias the jaw assembly 102 open by radially overlying the proximal extensions 148 proximal of the hinge pins 146, and the tubular member 114 may close the jaw assembly 102 by camming a portion of the jaw members 110, 112 distal of the hinge pins 146.

The proximal portion 154 of the tubular member 114 may be slideably received in the lumen 108 of the shaft 104. The proximal portion 154 may be secured to the actuator 150 by receiving the actuator 150 in a lumen of the proximal portion 154 and/or mating one or more radial projections of the actuator 150 with one or more proximal slots in or on the proximal portion 154. The proximal portion 154 may receive the proximal end of the connector 142 in a distal opening and include an elongated slot 160 along its length that receives a pin 162 on the connector 142. Longitudinal movement of the tubular member 114 relative to the connector 142 may cause the pin 162 to slide longitudinally through the elongated slot 160. The pin 162 may be fixedly secured (e.g., welded) to the shaft 104 to stabilize the connector 142. For example, the pin 162 may extend through and be welded into an elongated slot 164 of the shaft 104 that overlaps with the elongated slot 160 of the tubular member 114. The overlap of the elongated slots 160, 164 may allow visibility of the relative longitudinal position and/or movement of the tubular member 114 during actuation of the jaw assembly 102.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A clip applier configured to apply a surgical clip, the clip applier comprising:

a first jaw member and a second jaw member, the first jaw member being configured to pivot between an open configuration and a closed configuration;
a leaf spring configured to bias the first jaw member into the open configuration;
a tubular member configured to advance over the first jaw member to cam the first jaw member into a closed configuration against the bias of the leaf spring;
a shaft receiving a portion of the tubular member;
a handle assembly attached to a proximal end of the shaft;
a connector disposed in the tubular member, wherein the connector comprises a pin fixed to the shaft; and
an actuator extending through the shaft and actuated by the handle assembly,
wherein the actuator is configured to advance through the shaft to advance the tubular member over the first jaw member and the second jaw member.

2. The clip applier of claim 1, further comprising a second leaf spring configured to bias the second jaw member into an open configuration, wherein the second jaw member is configured to pivot between the open configuration and a closed configuration, and the tubular member is configured to advance over the second jaw member to cam the second jaw member into the closed configuration against the bias of the second leaf spring.

3. The clip applier of claim 2, wherein the leaf spring overlaps with a proximal portion of the first jaw member to bias the first jaw member into the open configuration, and the second leaf spring overlaps with a proximal portion of the second jaw member to bias the second jaw member into the open configuration.

4. The clip applier of claim 2, wherein the leaf spring and the second leaf spring are disposed on opposite lateral sides of the connector.

5. The clip applier of claim 2, wherein a proximal portion of the leaf spring and a proximal portion of the second leaf spring are fixed to the connector.

6. The clip applier of claim 1, wherein the proximal portion of each of the first and second jaw members includes a proximal extension angled relative to a longitudinal axis of the clip applier.

7. The clip applier of claim 6, wherein the proximal extension extends from only one lateral side of the respective first and second jaw member.

8. The clip applier of claim 1, wherein the first jaw member and the second jaw member each have a proximal portion and a distal portion, the proximal portion having a width less than the distal portion and configured to be received in the tubular member.

9. The clip applier of claim 1, wherein at least one of the first jaw member and the second jaw member are pivotably coupled to the connector.

10. The clip applier of claim 1, wherein the first jaw member is pivotably coupled to the connector at a first pivot pin, and the second jaw member is pivotably coupled to the connector at a second pivot pin.

11. The clip applier of claim 1, wherein the proximal portion of at least one of the first jaw member and the second jaw member straddles a distal portion of the connector.

12. The clip applier of claim 1, wherein the tubular member comprises a distal portion and a proximal portion, the distal portion has a larger diameter than the proximal portion, and the distal portion is configured to cam the first jaw member and second jaw member into the closed configuration.

13. The clip applier of claim 1, wherein the connector comprises a pin, the tubular member comprises an elongated slot, and the pin travels through the elongated slot as the tubular member advances.

14. A clip applier configured to apply a surgical clip, the clip applier comprising:
a first jaw member and a second jaw member, each configured to pivot between an open configuration and a closed configuration;
a first leaf spring overlapping a proximal portion of the first jaw member and configured to bias the first jaw member into the open configuration;
a second leaf spring overlapping a proximal portion of the second jaw member and configured to bias the second jaw member into the open configuration;
a tubular member configured to advance over the first jaw member and the second jaw member to cam the first jaw member and the second jaw member into the closed configuration against the bias of the first leaf spring and the second leaf spring;
a connector disposed in the tubular member, wherein the first leaf spring and the second leaf spring are disposed on opposite lateral sides of the connector;
a shaft; and
an actuator extending through the shaft, wherein the actuator is configured to advance through the shaft to advance the tubular member over the first jaw member and the second jaw member;
wherein the connector comprises a pin fixed to the shaft receiving the tubular member.

15. The clip applier of claim 14, wherein the first jaw member is pivotably coupled to the connector at a first pivot pin, and the second jaw member is pivotably coupled to the connector at a second pivot pin.

16. The clip applier of claim 14, wherein the tubular member comprises an elongated slot, and the pin travels through the elongated slot as the tubular member advances.

17. The clip applier of claim 14, wherein the tubular member comprises a distal portion and a proximal portion, the distal portion has a larger diameter than the proximal portion, and the distal portion is configured to cam the first jaw member and second jaw member into the closed configuration.

18. The clip applier of claim 14, further comprising:
a handle assembly on a proximal end of the shaft;
wherein the actuator is actuated by the handle assembly.

* * * * *